United States Patent
Cobani et al.

(10) Patent No.: US 11,903,845 B2
(45) Date of Patent: Feb. 20, 2024

(54) TIBIAL TRAY INSERTER

(71) Applicant: GLOBUS MEDICAL, INC., Audubon, PA (US)

(72) Inventors: Marius Cobani, Southampton, PA (US); Drew Mike, Phoenixville, PA (US); Jason Zappacosta, Philadelphia, PA (US); David Stumpo, Trappe, PA (US)

(73) Assignee: Globus Medical Inc., Audubon, PA (US)

(*) Notice: Subject to any disclaimer, the term of this patent is extended or adjusted under 35 U.S.C. 154(b) by 0 days.

(21) Appl. No.: 17/652,492

(22) Filed: Feb. 25, 2022

(65) Prior Publication Data

US 2023/0270563 A1 Aug. 31, 2023

(51) Int. Cl.
*A61F 2/46* (2006.01)
*A61F 2/38* (2006.01)
*A61F 2/30* (2006.01)

(52) U.S. Cl.
CPC .............. *A61F 2/461* (2013.01); *A61F 2/389* (2013.01); *A61F 2002/30133* (2013.01); *A61F 2002/30331* (2013.01); *A61F 2002/30884* (2013.01); *A61F 2002/4627* (2013.01)

(58) Field of Classification Search
CPC ....................... A61F 2/461; A61F 2/389; A61F 2002/30133; A61F 2002/30331; A61F 2002/30884; A61F 2002/4627
See application file for complete search history.

(56) References Cited

U.S. PATENT DOCUMENTS

| | | | |
|---|---|---|---|
| 5,732,992 A * | 3/1998 | Mauldin | A61F 2/461 606/205 |
| 5,733,290 A * | 3/1998 | McCue | A61F 2/4684 606/88 |
| 5,788,701 A * | 8/1998 | McCue | A61B 17/1604 606/88 |
| 6,520,966 B1 | 2/2003 | Kohler et al. | |
| 2008/0119941 A1 | 5/2008 | Seo et al. | |
| 2010/0241126 A1* | 9/2010 | Ghijselings | A61B 17/1725 606/88 |
| 2017/0266015 A1* | 9/2017 | Overes | A61F 2/4611 |
| 2019/0269422 A1* | 9/2019 | Metzger | A61F 2/4637 |
| 2022/0061998 A1* | 3/2022 | Zappacosta | A61F 2/461 |

FOREIGN PATENT DOCUMENTS

| | | | |
|---|---|---|---|
| CN | 201701333 U | 1/2011 | |
| CN | 209827110 U | 12/2019 | |
| CN | 112618115 A | 4/2021 | |
| EP | 0780090 A1 | 6/1997 | |
| EP | 2649967 A1 * | 10/2013 | ......... A61B 17/1764 |
| EP | 4082485 A1 * | 11/2022 | |

* cited by examiner

*Primary Examiner* — Megan Y Wolf

(57) ABSTRACT

Tibial implants, instruments, systems, and methods of implanting a tibial tray during a knee arthroplasty. The inserter instrument may include a main body with a pair of fixed posterior tabs, a moveable anterior tab body with an anterior tab, and a rotatable shaft for controlling movement of the anterior tab body. When the shaft is rotated, the anterior tab body is translated into an expanded position to lock the inserter to the tibial tray, thereby providing precise positioning of the tibial tray during implantation.

10 Claims, 15 Drawing Sheets

TIBIAL TRAY INSERTER

FIELD OF THE INVENTION

The present application relates generally to knee arthroplasty, and more particularly, to knee arthroplasty instruments, implants, and methods of installing knee arthroplasty implants.

BACKGROUND OF THE INVENTION

Knee arthroplasty, often called a knee replacement, is a surgical procedure used to reconstruct and resurface a knee that has been damaged, for example, by arthritis. Total knee arthroplasty (TKA) devices may replace both the tibiofemoral joint and the patellofemoral joint. The tibiofemoral joint is where the tibia and the femur articulate. The patellofemoral joint is where the patella and the femur articulate. To replace the tibiofemoral joint, the knee arthroplasty may include a femoral trial (or implant) secured to the distal end of the femur, a tibial tray (or implant) secured to the proximal end of the tibia, and an insert disposed therebetween. The femoral and tibial implants cap the ends of the femur and tibia, respectively, which form the knee joint, thereby reconstructing the knee. To replace the patellofemoral joint, the knee arthroplasty may include a patella prostheses (or implant) to replace the backside of the patella and form a replacement articulating surface which interfaces with the femoral trial or implant.

The tibial portion of the procedure may include a planar resection to the proximal tibia, which is replaced with a tibial implant assembly including a tibial tray and an articulating spacer insert. The tibial tray may include a keel structure to offer additional support and fixation to the cancellous bone of the tibia. A keel punch may be utilized to create the initial cavity to allow for the keel of the tibial tray to seat into the resected tibia. The placement of the tibial tray, although partially predetermined by the keel punch cavity, may be slightly altered by the surgeon when implanting the tibial tray. There exists a need for improved tibial trays and inserter instruments configured to implant the trays, which allow for control over six degrees of freedom of movement and precise placement of the tibial tray during implantation.

SUMMARY OF THE DISCLOSURE

To meet this and other needs, implants, instruments, systems, and methods of installing tibial tray implants are provided. In particular, inserter instruments may be configured to lock to the tibial tray with one or more locking mechanisms. For example, the tibial tray may include one or more pockets configured to receive corresponding tabs on the inserter. One anterior tab on the inserter may be slidable to engage and disengage with one of the pockets in the tibial tray. The tibial tray is attachable to the inserter to offer improved control of movement with six degrees of freedom. In this way, the surgeon may adjust placement of the tibial tray based on surgeon preference and desired patient outcome. The inserter may also be used to extract the tibial tray during a revision procedure. The implant may further include an insert, which is attachable to the tibial tray via the same pockets used for the inserter.

According to one embodiment, a system for a knee arthroplasty includes a tibial tray and an inserter. The tibial tray has a perimeter wall defining an insert-receiving space, and the perimeter wall defines a pair of posterior notches/undercut and a single anterior notch/undercut. The inserter has a main body with a pair of fixed posterior tabs, a moveable anterior tab body having an anterior tab, and a rotatable shaft for controlling movement of the anterior tab body. The posterior tabs are receivable in the posterior notches of the tibial tray and the anterior tab is receivable in the anterior notch of the tibial tray when the shaft is rotated and the anterior tab body is translated into an expanded position.

The system may include one or more of the following features. The tibial tray may have a kidney-bean shape with an anterior side forming an outer convex side and a posterior side including an inner concave side separating two lobes. The tibial tray may include a keel attached to a distal surface of the tibial tray, and the keel may include a pair of coronal fins and a pair of sagittal fins. In a cementless procedure, the tibial tray may also include a plurality of pegs attached to the distal surface of the tibial tray. The main body of the inserter may include a foot with a neck protruding upwardly and an arm protruding anteriorly. The foot may be bifurcated by a keyway such that the anterior tab body is receivable in the keyway. The anterior tab body may include a pair of keyway wings projecting outwardly in opposite directions. The keyway may define recesses configured to receive the respective keyway wings, thereby preventing anterior-posterior angulation while expansion occurs. The inserter may include a plurality of plugs press fit into the main body and the anterior tab body. The plugs may be secured with transverse dowel pins extending through the plug body. The plugs may protrude from a bottom of the main body, thereby ensuring the main body does not contact or damage the insert-receiving space of the tibial tray.

According to one embodiment, an inserter instrument for implanting a tibial tray includes a main body, a moveable anterior tab body, and a rotatable shaft. The main body is coupled to a handle. The main body includes a pair of posterior tabs. The moveable anterior tab body is located inside the main body. The anterior tab body includes a threaded opening and an anterior tab. The rotatable shaft controls movement of the anterior tab body. The shaft has a threaded portion engaged with the threaded opening in the anterior tab body. The shaft is positioned through the main body and the anterior tab body. When the shaft is rotated, the anterior tab body is translated outside the main body into a locked position.

The inserter instrument may include one or more of the following features. The main body may include a foot with a neck protruding upwardly and an arm protruding anteriorly. The foot may have an outer kidney-bean shape. The foot may be bifurcated by a keyway, and the anterior tab body may be receivable in the keyway. The anterior tab body may include a pair of keyway wings projecting outwardly in opposite directions. The keyway may define recesses configured to receive the respective keyway wings, thereby preventing anterior-posterior angulation while expansion occurs. The anterior tab body may include a base with an upwardly projecting tongue defining the threaded opening. The threaded opening may be a triple lead threaded hole, and the shaft may include a triple lead shaft configured to interface with the triple lead threaded hole to increase translation speed of the anterior tab body. The anterior tab may be positioned along an anterior portion of the base, and the anterior tab may extend along the entire width of the anterior tab body. The handle may include an elongate body that terminates distally at a threaded end, and the threaded end may mate with corresponding threads in the main body.

According to another embodiment, a method for implanting a tibial implant includes one or more of the following steps in any suitable order: (1) positioning fixed posterior tabs on a main body of an inserter into corresponding posterior notches in a perimeter wall of a tibial tray; (2) tilting the tibial tray until a foot of the main body of the inserter is received in an insert-receiving space of the tibial tray; (3) rotating a shaft through the main body of the inserter to translate an anterior tab body and expand an anterior tab into an anterior notch in the tibial tray, thereby locking the inserter to the tibial tray; and (4) moving the tibial tray to a desired position and implanting the tibial tray into a proximal tibia of a patient. The inserter may be configured to move the tibial tray with internal/external rotation, proximal/distal translation, anterior/posterior translation, anterior/posterior angulation, medial/lateral translation, and varus/valgus angulation. The method may include, before positioning the inserter, resecting the proximal tibial to form a planar resection surface and/or punching a cavity into the proximal tibia, and the cavity may be configured to receive a keel of the tibial tray. After removing the inserter, an insert may be attached with tabs receivable in the same posterior and anterior notches in the tibial tray.

Also provided are kits including implants or implant trials of varying types and sizes including tibial trays and inserts that vary in anterior-posterior (AP) and/or medial-lateral (ML) aspects, instruments of varying types and configurations including lockable inserter instruments, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Embodiments of the disclosure are generally directed to implants, instruments, systems, and methods for implanting a tibial tray, for example, during a total knee arthroplasty. Specifically, embodiments are directed to instruments and systems configured to lock the inserter instrument to the tibial tray to provide for enhanced control and maneuverability of the tibial tray during implantation. The inserter instrument may utilize the same locking features as the insert, such as one or more pockets or notches in the tibial tray that receive one or more corresponding tabs. The inserter instrument may include the moveable anterior tab to provide a rigid locking mechanism to the tibial tray.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments and modifications thereof are contemplated as falling within the scope of this disclosure and equivalents thereto.

Figure 1:
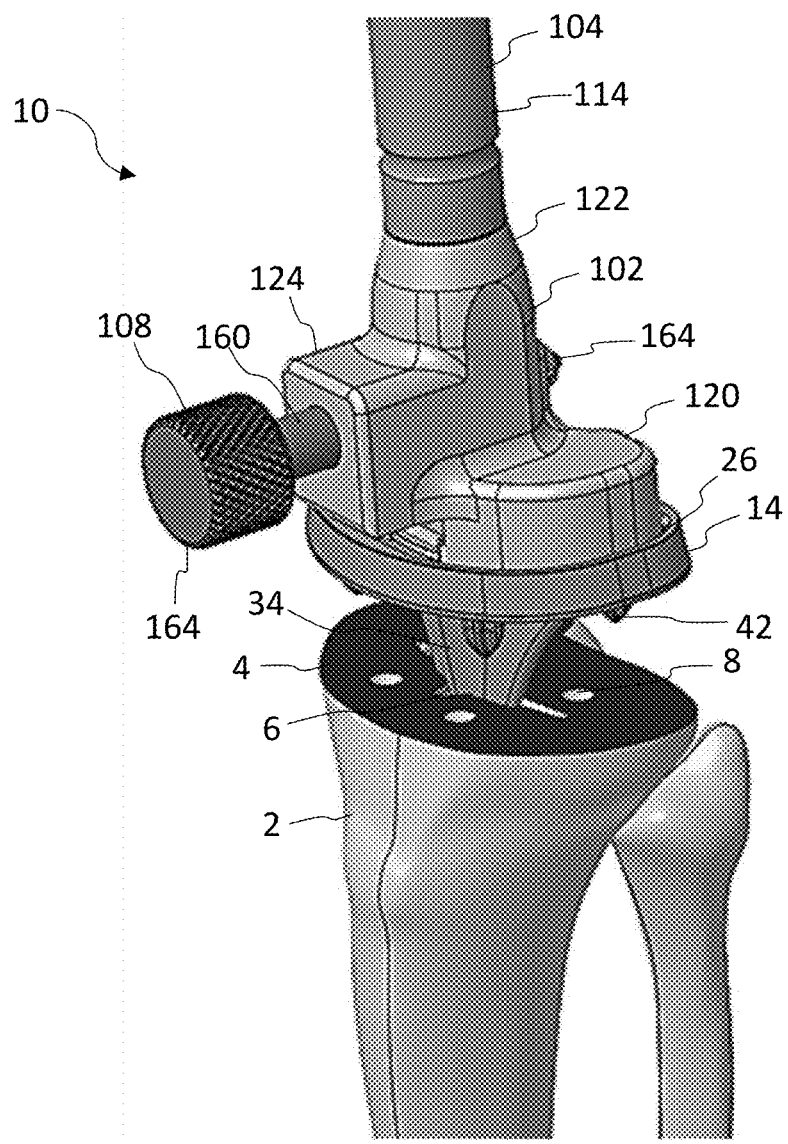
FIG. 1 shows a perspective view of an inserter instrument locked to a tibial tray for implanting the tibial tray into a resected portion of the proximal tibia of a patient according to one embodiment.

Referring now to FIG. 1, an inserter instrument 10 is attached to a tibial tray 14 for implanting the tibial tray 14 at the proximal end of a tibia 2 of a patient according to one embodiment. During a total knee arthroplasty (TKA), a planar resection 4 may be made to the proximal tibia 2 and replaced with a prosthesis or tibial tray implant 14. The tibial tray 14 may be offered in multiple sizes that vary in the anterior-posterior (AP) and medial-lateral (ML) aspects in order to conform to patient anatomy. The tray 14 may include a keel structure 34 on the distal surface 24 of the tray 14, as well as one or more optional pegs 42 (for example, in a cementless setting) which offer additional support/fixation to the cancellous bone of the tibia 2. A keel punch (not shown) may be utilized to create initial cavity 6 within the cancellous bone of the tibia 2 to allow for the keel 34 of the tibial tray 14 to seat into the proximal tibia 2. One or more additional openings 8 may be created in the resection 4 to allow for receipt of the pegs 42. After all required preparation of the tibia 2 has taken place, the tibial tray 14 is implanted into the resected 4 and punched 6 proximal tibia 2. The tibial tray 14 may be impacted into place to ensure proper seating of the tray 14 has occurred. After the tray 14 is installed and inserter 10 removed therefrom, insert 16 may be connected to the tray 14 to complete the tibial implant assembly 12.

The placement of the tibial tray 14, although predetermined by the keel punch cavity 6 made during tibial preparation, may be slightly altered based on the surgeon's preference when implanting the tray 14. These alterations may be based on the surgeon's feel and preference when in the process of implanting the tray 14 or other parameters. For the surgeon to make precise adjustments, the tibial tray 14 is attached and locked to inserter 10 which offers control over up to six degrees of freedom of movement. Furthermore, during a revision procedure, the inserter 10 may also be used to extract and remove the tibial tray 14, by for example using a slap hammer threadably received in the inserter handle.

Although generally described with reference to a knee arthroplasty, it will be appreciated that the instruments, implants, and systems described herein may be applied to other orthopedic locations and applications, such as the spine including between vertebrae, long bones, such as a femur, a tibia, a humerus, a clavicle, a fibula, an ulna, a radius, bones of the foot, bones of the hand, or other suitable bone(s) or joints.

Figure 2:
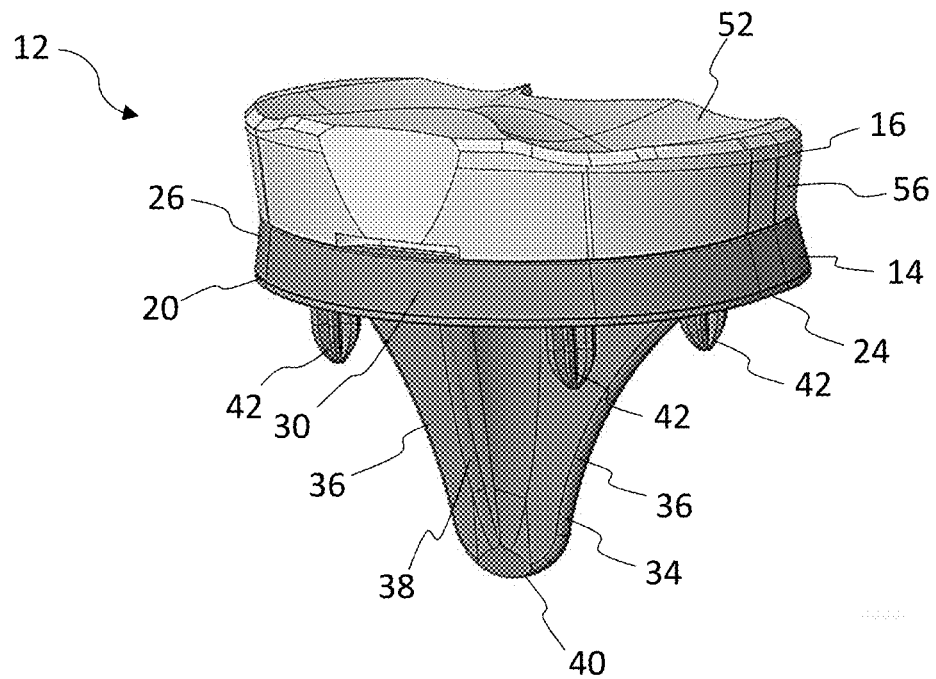
FIG. 2 shows an assembled anterior perspective view of the insert and tibial tray according to one embodiment.
Figure 3:
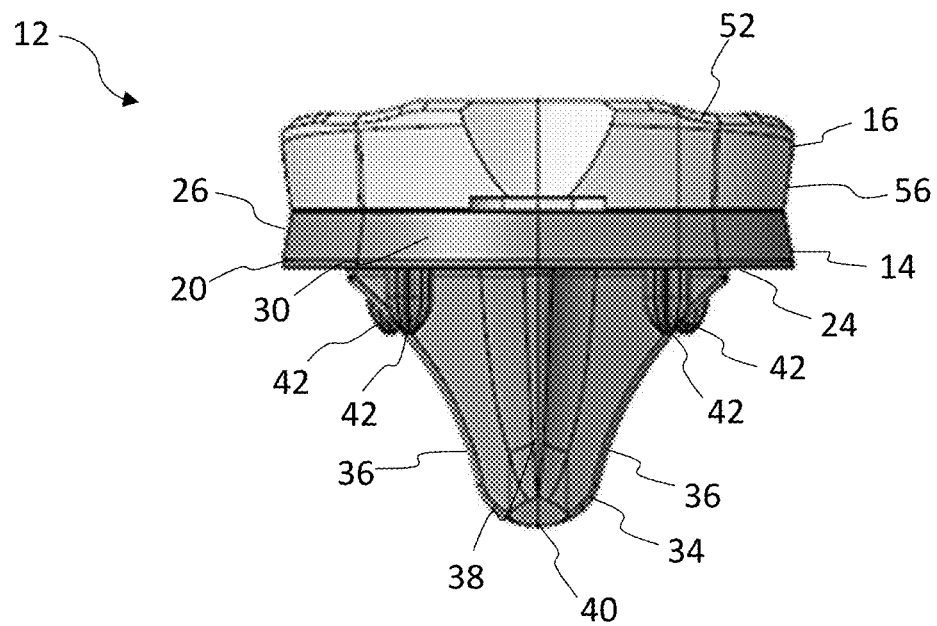
FIG. 3 is an anterior view of the insert and tibial tray assembly according to one embodiment.

Turning now to FIGS. 2-9, tibial implant assembly 12 is described in further detail. FIGS. 2 and 3 show the tibial implant assembly 12 including tibial tray 14 sized and shaped for placement on the proximal end of tibia 2 of a patient and a liner or insert 16 receivable into tray 14. The insert 16 includes an articulating or articular surface 52 configured to interface with a femoral implant (not shown). The insert 16 sits between the tibial tray 14 and the femoral implant to mimic the motion of a natural knee and provide support as the knee is bent and flexed. Basically, it balances the joint space and provides an articulating surface as the knee goes through physiologic range of motion.

The implant assembly 12 may be comprised of one or more biocompatible materials. For example, the tibial tray 14 may be made from a metal, such as titanium, stainless steel, Cobalt chrome, carbon composite, or suitable alloys. The insert 16 may be made from a plastic or polymer, such as polyethylene, ultra-high molecular weight polyethylene (UHMWPE), polyetheretherketone (PEEK), or combinations of such materials. The femoral implant may also be made from a metal/metal alloy, such as cobalt chrome or titanium. In this manner, the components are configured so that metal articulates against plastic in order to provide smooth movement and minimal wear. These materials may be machined, casted, constructed from additive manufacturing, such as 3D printing, subtractive manufacturing, or hybrid manufacturing processes. Although the materials described herein are exemplified, it will be appreciated that any suitable materials and construction may be selected for the individual components.

Figure 4:
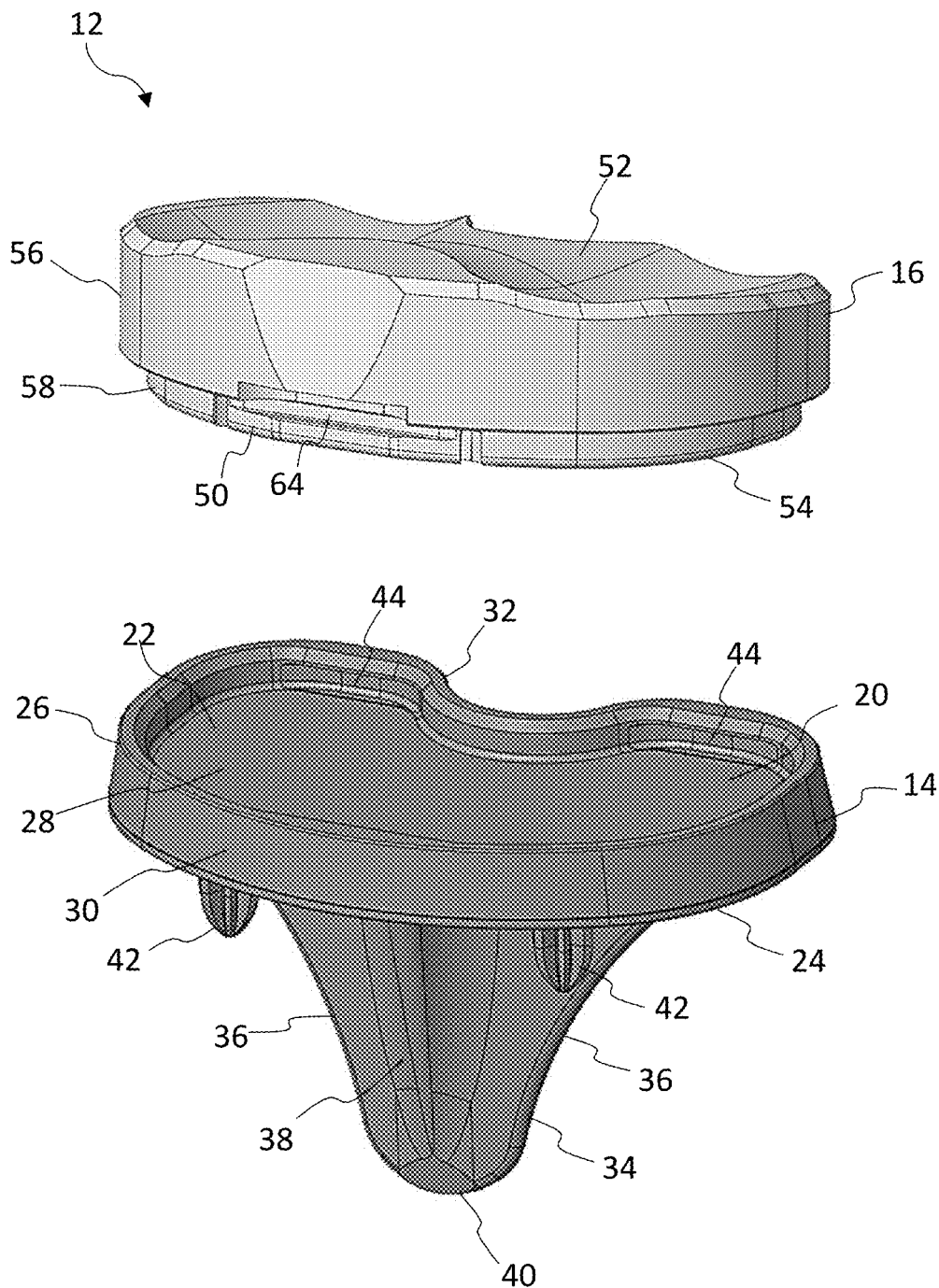
FIG. 4 shows an exploded perspective view of the insert and tibial tray from an anterior perspective.
Figure 5:
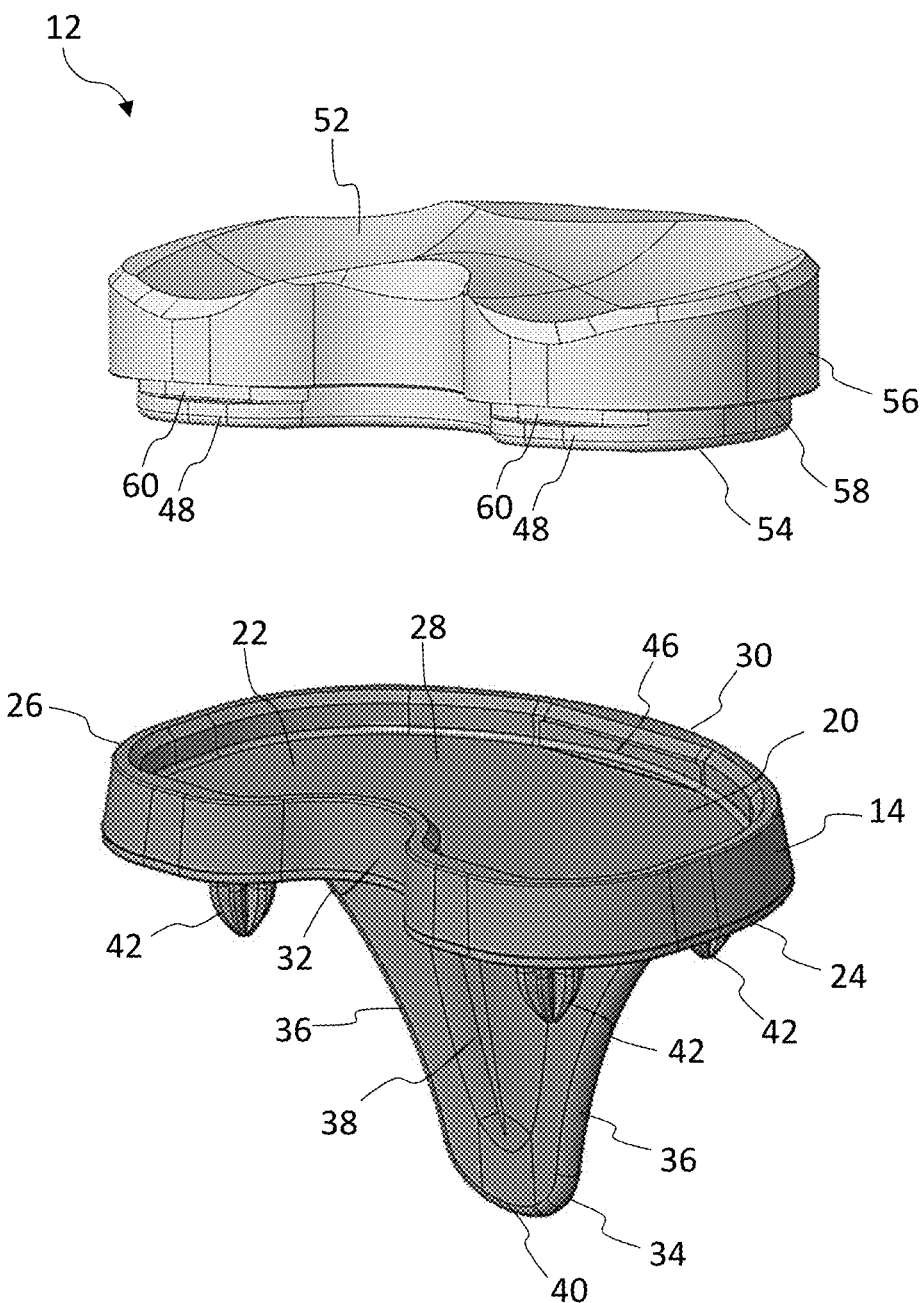
FIG. 5 shows an exploded perspective view of the insert and tibial tray from a posterior perspective.

With further emphasis on FIGS. 4 and 5, the tibial tray 14 includes a plate 20 including opposite proximal and distal surfaces 22, 24. The distal surface 24 of the tibial plate 14 is configured to engage the resected surface 4 of the tibia 2. The tibial plate 20 has a perimeter edge, wall, or lip 26 defining an insert-receiving space 28 sized and shaped to receive the insert 16. The proximal surface 22 of the plate 20 defines the distal or bottom surface of the insert-receiving space 28.

The tibial plate 14 includes an anterior side 30 and an opposite posterior side 32. The outer profile of the tibial tray 12 may be rounded or curved. For example, the tibial tray 12 may have the general shape of a long oval indented at one side, such as a kidney-bean shape. The anterior side 30 may form an outer convex side as one long side and the posterior side 32 may include an inner concave side separating two lobes or rounded ends. It will be appreciated that the tibial plate 20 and lip 26 may generally have any suitable size and shape configured to match the particular size and shape of the proximal end of the tibia 2 of the patient.

The tibial implant 12 may include a tibial stem or keel 34. The tibial keel 34 is configured to be inserted into the punched cavity 6 in the resected surface 4 at the proximal end of the tibia 2 of the patient. The tibial keel 34 is attached to the distal surface 24 of the tibial plate 20. The tibial keel 34 extends generally distally from the distal surface 24 of the tibial plate 20. The tibial keel 34 may be solid or hollow (e.g., have a solid or hollow core).

The tibial keel 34 may include one or more fins 36, 38 including coronal fins 36 and/or sagittal fins 38. The coronal fins 36 (e.g., two fins 36) may extend outward from the center of the tibial keel 34 in a direction that is generally parallel to a coronal plane of the patient (e.g., a vertical side-to-side extending plane). The coronal fins 36 may be provided at a slight angle relative to the coronal plane, for example, about 15 degrees or less to form a slight V-shape. The sagittal fins 38 (e.g., two sagittal fins) may extend outward from the center of the tibial keel 34 in a direction that is generally parallel to a sagittal plane of the patient (e.g., a vertical front-to-rear extending plane). The coronal and sagittal fins 36, 38 may taper inwardly or narrow as the fins 36, 38 extend distally. The width of the sagittal fin 38 may also taper inwardly (e.g., in a direction generally parallel to the coronal plane) as the fin 38 extends distally. The fins 36, 38 may have rounded edges to improve insertion into the cavity 6. The distal-most nose or tip 40 of the tibial keel 34 may be tapered or curved, for example, along the coronal plane and/or the sagittal plane. It will be appreciated that other configurations or modifications to the tibial keel 34 may be provided to enhance insertion and retention within cavity 6 in the proximal tibia 6.

The tibial tray 14 may further include at least one anchoring projection or peg 42. Each peg 42 is configured to be inserted into corresponding openings 8 in the resection 4 of the proximal tibia 2 of the patient. The pegs 42 may be provided on the tray 14, for example, in a cementless procedure to provide addition support and/or fixation to the cancellous bone of the tibia 2. It will be appreciated that the tibial tray 14 may be implanted with or without cement. The pegs 42 extend generally distally from the distal surface 24 of the tibial plate 14. The pegs 42 may have a generally rounded or conical shape (e.g., a bullet shape) or other suitable shapes may be used. The pegs 42 may include one or more peripheral ribs, for example, with rounded, chamfered, sharpened, or fillet edges. The ribs may be configured to minimize bone displacement, the risk of fracture, and/or increase the surface area for bone ingrowth. The pegs 42 may be solid or hollow (e.g., have a solid or hollow core). The pegs 42 may be spaced apart from one another about the distal surface 24 of the tibial plate 20. For example, the pegs 42 may be arranged around the tibial keel 34 with the tibial keel 34 positioned centrally between the pegs 42. Any suitable quantity and arrangement of the pegs 42 may be provided to achieve the desired support and fixation to the tibial tray 14. The pegs 42 may be generally identical to one another or may be otherwise configured.

The tibial implant assembly 12 may form part of a fixed bearing knee replacement where insert 16 is fixed to the tibial tray 14. For example, the insert 16 may snap fit into the insert-receiving space 28 with one or more locking members. As illustrated, the insert 16 may lock to the tray 14 with one or more interlocking tabs 48, 50 and notches 44, 46. The perimeter wall 26 of the tray 14 may define one or more recesses, pockets, or notches 44, 46 used to receive a portion of the insert 16 to hold the insert 16 in the insert-receiving space 28 of the tibial tray 14.

The insert 16 includes a body with an upper articular surface 52 and an opposite lower surface 54 configured to be received in the insert-receiving space 28 in the tibial tray 14. The upper articular surface 52 may be recessed and contoured to articulate with a femoral component or implant (not shown). The lower surface 54 is configured to contact the proximal face 22 of the tibial plate 20. The outer wall 56 of the insert 16 may have the general shape of a long oval indented at one side, such as a kidney-bean shape, which generally corresponds to the outer shape of the tibial tray 14. A distal portion of the insert 16 defines an indented collar 58 receivable in the insert receiving space 28 in the tibial tray 14. The collar 58 defines one or more tabs 48, 50 configured to engage with the corresponding pockets or notches 44, 46 in the tibial tray 14. The tab 48, 50 may be defined by one or more slits or relief cuts to form a resilient tab.

The insert 16 may include a pair of posterior tabs 48 positioned along the posterior portion of the insert 16 and a single anterior tab 50 positioned along the anterior portion of the insert 16. As best seen in FIG. 5, the posterior tabs 48 may be located on the two lobes separated by the inner concavity. The posterior tabs 48 may each be elongated with a length extending in a direction that is generally parallel to a coronal plane of the patient (e.g., a vertical side-to-side extending plane). The posterior tabs 48 are receivable in the corresponding posterior pockets or notches 44 in the tray 14. As best seen in FIG. 4, the anterior tab 50 may be located centrally on the convex side of the insert 16. The anterior tab 50 may also be elongated with a length extending in a direction that is generally parallel to a coronal plane of the patient. The anterior tab 50 may be generally longer than each of the posterior tabs 48. The anterior tab 50 is receivable in the corresponding anterior pocket or notch 46 in the tray 14.

The tibial trays 14 may utilize three pockets 44, 46 to allow tabs 48, 50 on the polyethylene (poly) insert 16 to lock into the tray 14. The posterior tabs 48 fasten to the posterior pockets 44 of the tibial tray 14. The two pockets 44 located on the posterior of the tibial tray 14 may shift slightly in the medial-lateral aspect as the trays 14 increase in size. The single pocket 46 located on the anterior of the tray 14 may shift more significantly in the anterior-posterior aspect. These tabs 48, 50 may be the only way to fasten the poly insert 16 or any instrument that may work in tandem with the tray 14.

Figure 6:
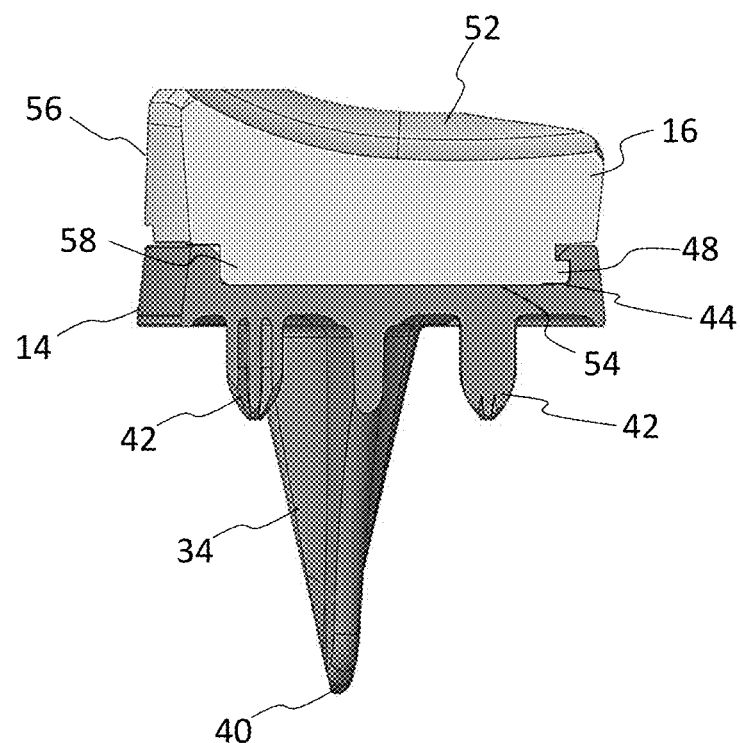
FIGS. 6 and 7 show cross-sectional and close-up views of the insert interlocked with the tibial tray including the posterior tab locking mechanism according to one embodiment.
Figure 7:
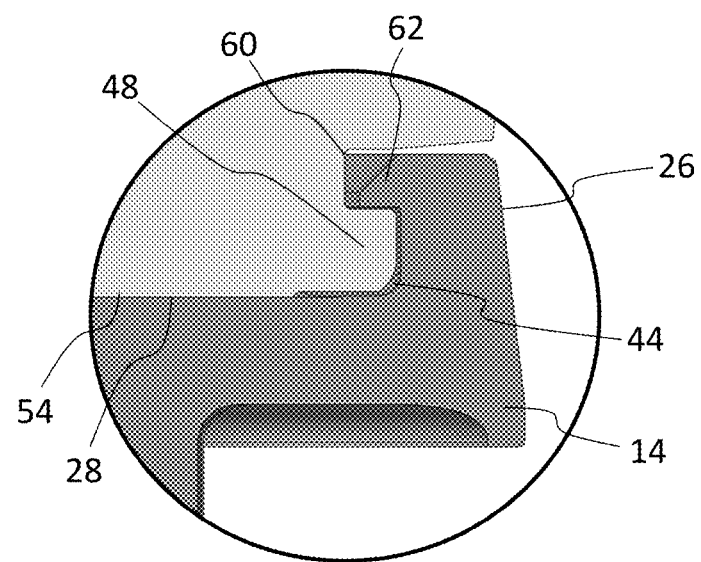

With further emphasis on FIGS. 6 and 7, the interlocking of posterior tab 48 with posterior notch 44 is shown in greater detail. The collar 58 may define a recess 60 proximal to the tab 48. The recess 60 may be configured to receive an inward lip 62 projecting from the edge 26 of the tray 14. An upper surface of the lip 62 may be generally planar or flat. In this manner, when the collar 58 is received in the insert-receiving space 28 in the tray 14, the posterior tab 48 is received in notch 44 and the lip 62 is received in recess 60, thereby securing the posterior portions of the insert 16 to the tibial tray 14.

Figure 8:
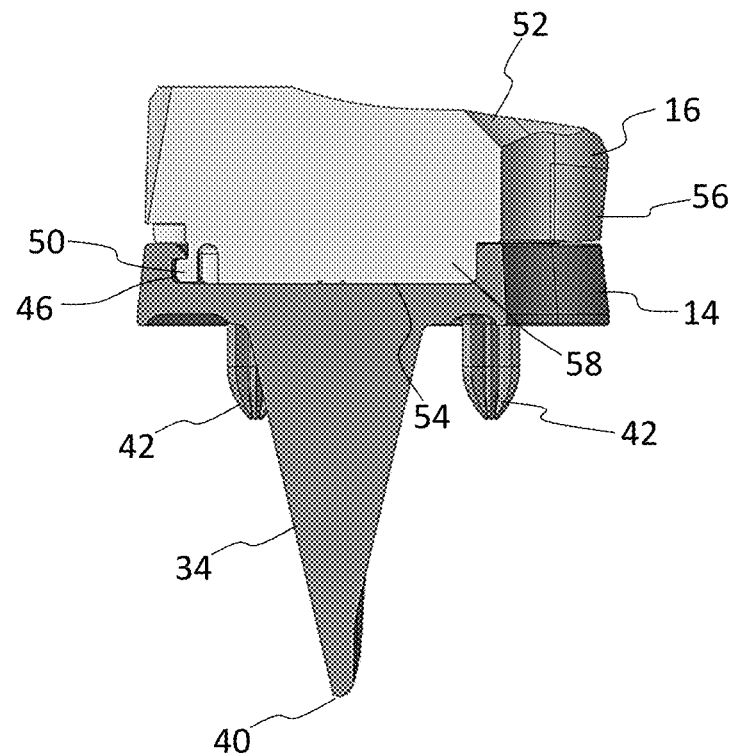
FIGS. 8 and 9 show cross-sectional and close-up views of the insert interlocked with the tibial tray including the anterior tab locking mechanism according to one embodiment.
Figure 9:
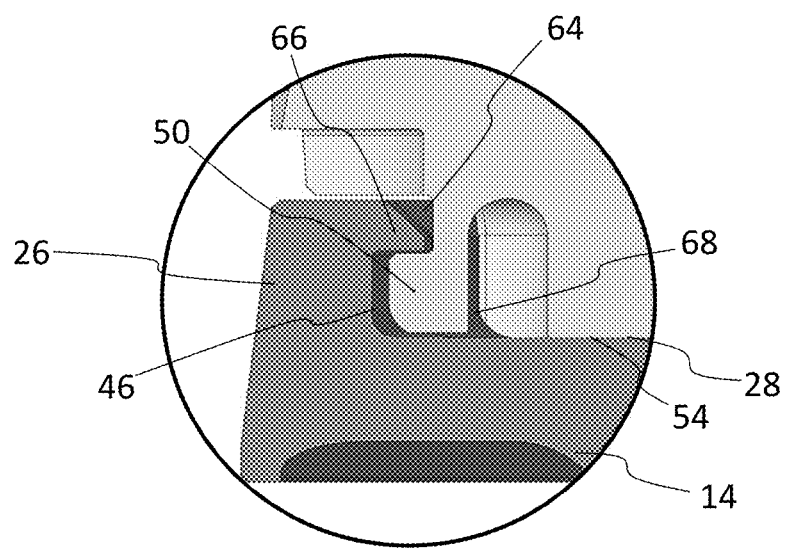

With further emphasis on FIGS. 8 and 9, the interlocking of anterior tab 50 with anterior notch 46 is shown in greater detail. The collar 58 may define a recess 64 above and proximal to the tab 50. The recess 64 may be configured to receive an inward lip 66 projecting from the edge 26 of the tray 14. The lip 66 may define a bevel or chamfer on an upper surface along the leading end of the lip 66 to aid insertion into recess 64. A relief cut 68 may be provided behind the anterior tab 50 to allow for further flexibility and resiliency of the anterior tab 50. In this manner, when the collar 58 is received in the insert-receiving space 28 in the tibial tray 14, the anterior tab 50 is received in notch 46 and the lip 66 is received in recess 64, thereby locking the anterior aspect of the insert 16 to the tibial tray 14.

Turning now to FIGS. 10-25, the inserter instrument 10 may utilize the same interlocking tab and existing notch 44, 46 configuration as the insert 16 to lock the inserter 10 to the tibial tray 14. The lockable functionality of the inserter instrument 10 to the tibial tray 14 allows for control over six degrees of freedom of movement and precise placement of the tibial tray 14 during implantation. The six degrees of freedom may include internal/external rotation, proximal/distal translation, anterior/posterior translation, anterior/posterior angulation, medial/lateral translation, and varus/valgus angulation.

Figure 10:
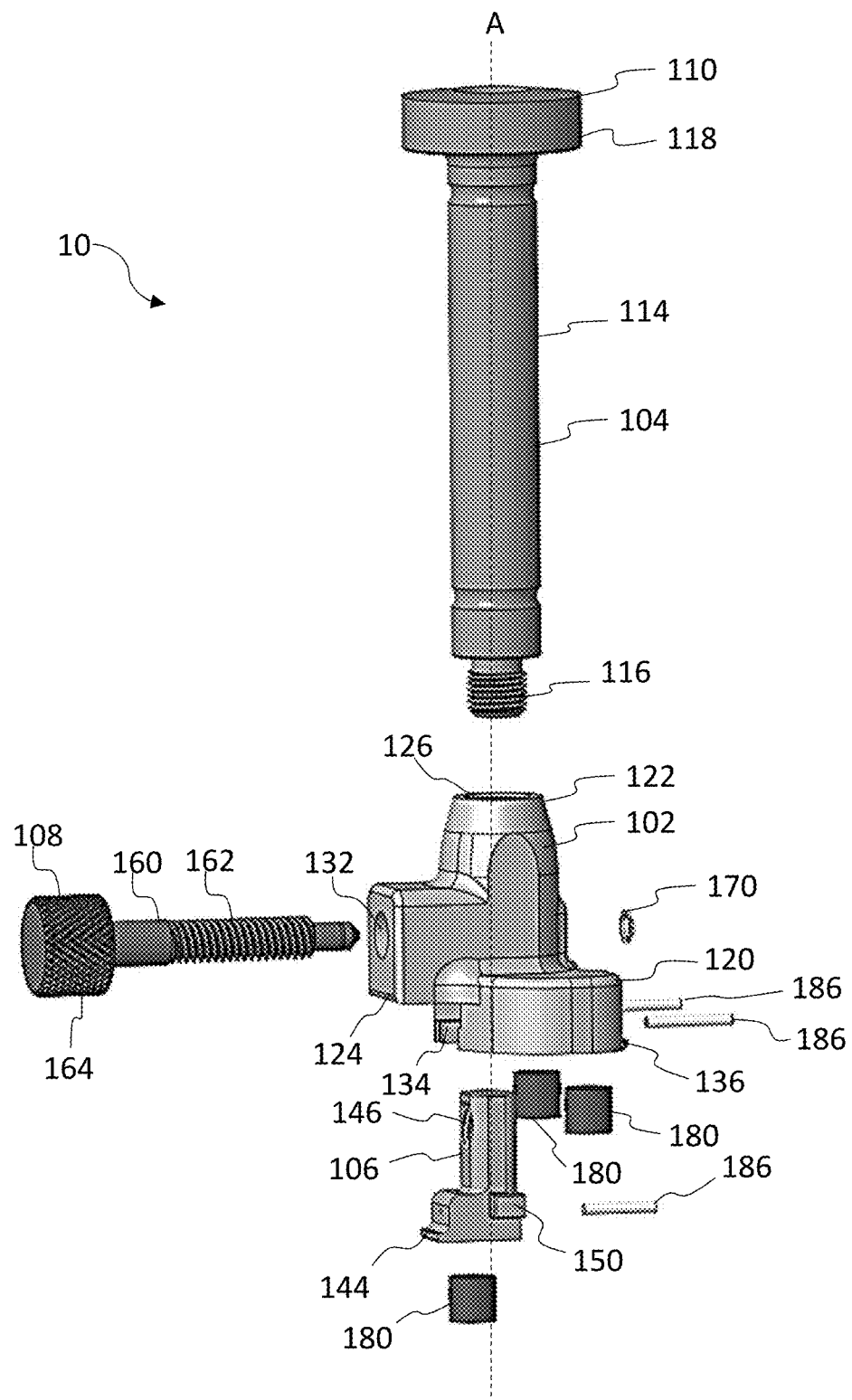
FIG. 10 shows an exploded view of the inserter instrument according to one embodiment.

With emphasis on FIG. 10, the inserter instrument 10 includes a main body 102 coupled to a handle 104 and a moveable anterior tab body 106 inside the main body 102. The anterior tab body 106 is controllable by a rotatable shaft 108, which expands the anterior tab body 106 from the main body 102 to thereby lock the inserter 10 to the tibial tray 14. The inserter instrument 10 extends from a proximal end 110 to a distal end 112 along a central longitudinal axis A. The proximal end 110 includes handle 104 which is grippable and controllable by a user. The distal end 112 includes main body 102 which is configured to engage with the tibial tray 14 to thereby control movement of the tibial tray 14 during impaction and insertion.

The handle 104 may be generally aligned along the central longitudinal axis A of the instrument 10. The handle 104 may include an elongate body 114 that terminates distally at a threaded end 116. In the embodiment shown, the elongate body 114 may be generally cylindrical in shape and may have a hollow or central channel therethrough. The threaded end 116 may include one or more threads configured to mate with corresponding threads 128 in the main body 102. The corresponding threads 128 are also suited to be directly attached to a slap hammer as opposed to a generic instrumentation handle if desired. The threaded end 116 of the handle 114 may have a reduced diameter relative to the outer diameter of the elongate body 114. The proximal end 110 of the handle 104 may include an enlarged head 118 with an outer diameter greater than the outer diameter of the elongate body 114. The enlarged head 18 may be configured to be struck by an impaction instrument, such as a mallet. It will be appreciated that the handle 104 may include a generic instrumentation handle or may be otherwise configured for manipulation by the user. The handle 104 may also include a threaded feature at end 110 that allows for a slap hammer to be attached.

Figure 11:
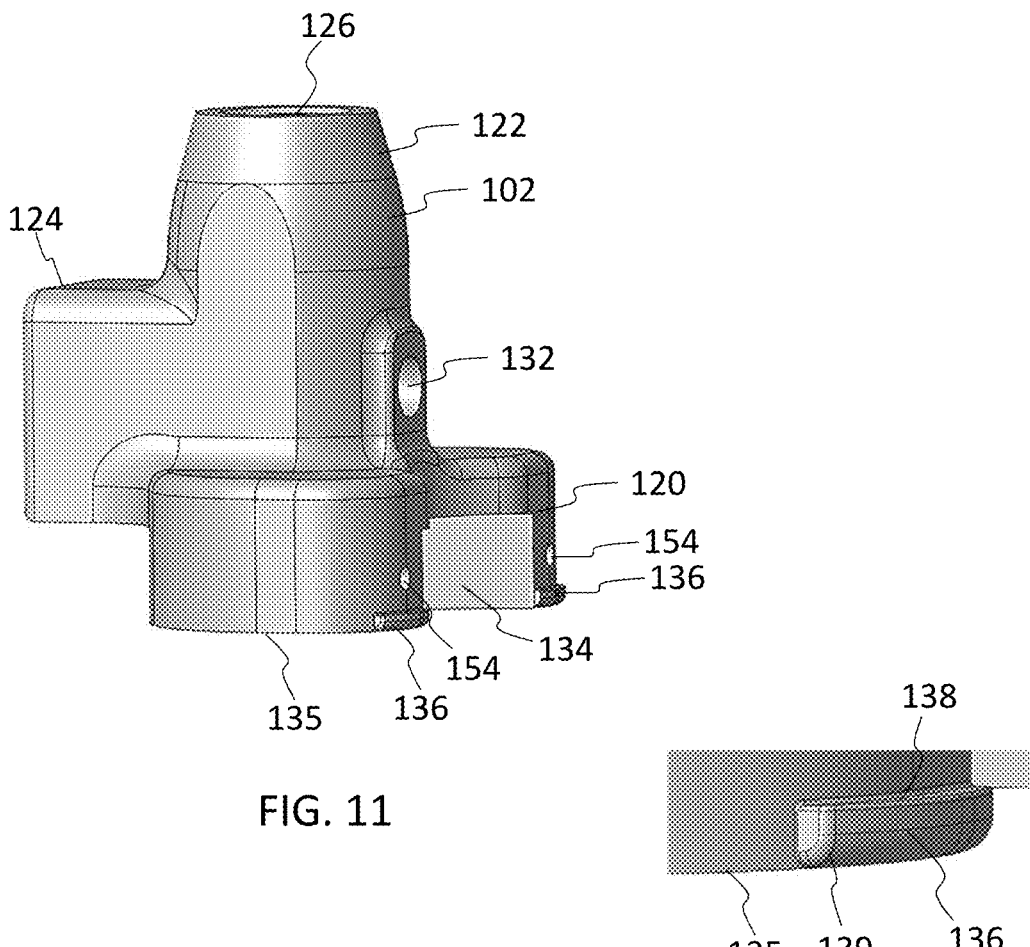
FIG. 11 is a perspective view of the main body of the inserter instrument according to one embodiment.
Figure 12:
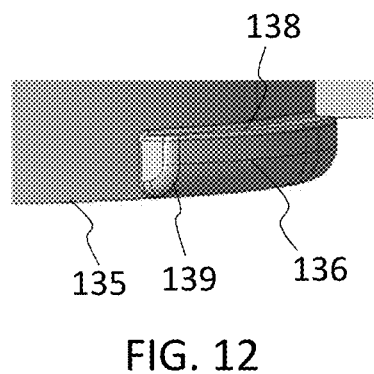
FIG. 12 is a close-up view of a fixed posterior tab on the main body of the inserter instrument according to one embodiment.
Figure 13:
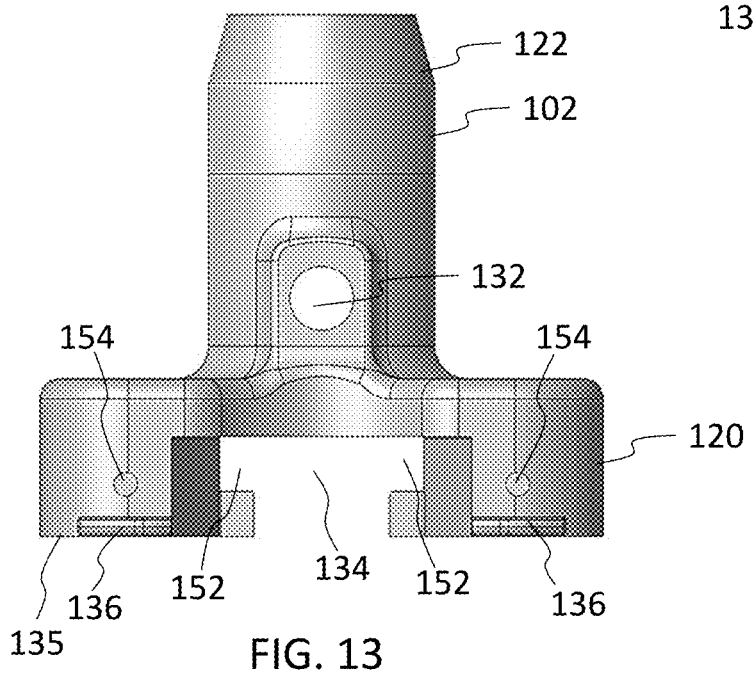
FIG. 13 shows a posterior view of the main body of the inserter instrument with a keyway for receiving the moveable anterior tab body according to one embodiment.

With emphasis on FIGS. 11-13, the main body 102 includes a base or foot 120 with a neck 122 protruding upwardly or proximally and an arm 124 protruding anteriorly. The neck 122 defines a central opening 126 with one or more internal threads 128. The neck 122 and central opening 126 may be generally aligned along the central longitudinal axis A of the instrument 10. When the threaded end 116 of the handle 114 is threaded into opening 126, the handle 114 is secured to the main body 102. It will be appreciated that other ways of attachment including press-fit, adhesive, pins, or the like may be used to secure the handle 114 to the main body 102.

The base or foot 120 is generally sized and shaped to fit within the insert-receiving space 28 in the tibial tray 14. In other words, the outer wall of the foot 120 may have the same kidney-bean shape, which generally corresponds to the indentation 28 in the tray 14. The foot 120 may be bifurcated by a keyway 134 configured to receive a portion of the anterior tab body 106. The keyway 134 may include one or more grooves or recesses 152 configured to receive corresponding keyway wings 150 on the anterior tab body 106. The foot 120 may include one or more posterior tabs 136 positioned along the posterior portion of the foot 120. The posterior tabs 136 may be fixed to the foot 120. The posterior tabs 136 may be located on the two lobes separated by the keyway 134. The posterior tabs 136 may each be elongated with a length extending in a direction that is generally parallel to a coronal plane of the patient (e.g., a vertical side-to-side extending plane). The posterior tabs 136 are receivable in the corresponding posterior pockets or notches 44 in the tibial tray 14. The posterior tab 136 may have a generally flat or planar upper surface 138 and a rounded or curved lower surface 139. The posterior tabs 136 may have the rounded bottom 139 transition to the planar top 138 to hook into the corresponding notches 44 in the tibial tray 14.

Figure 20:
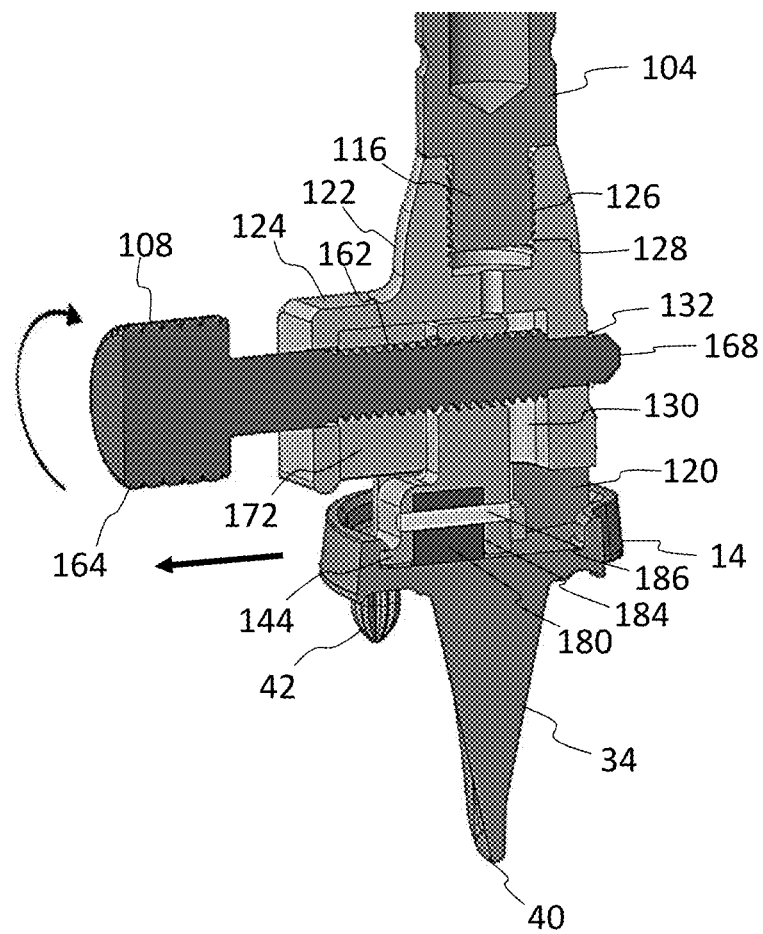
FIG. 20 shows a cross-sectional view of the inserter with the anterior tab extended thereby locking the inserter to the tibial tray.
Figure 21:
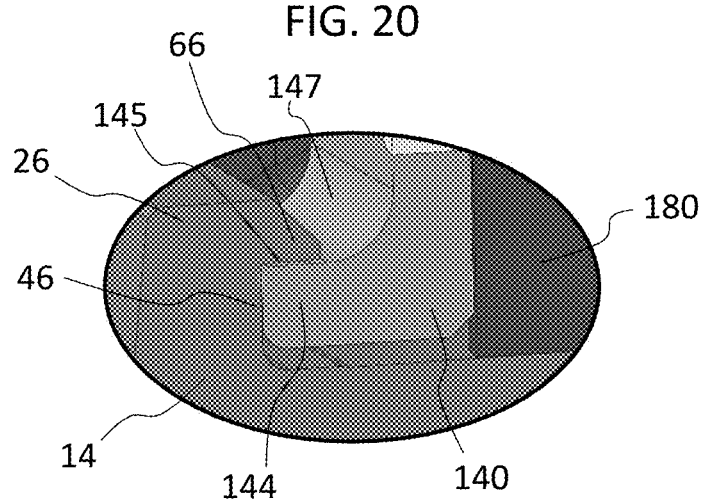
FIG. 21 is a close-up cross-sectional view of the anterior tab of the inserter engaged with the tibial tray.

The foot 120 and arm 124 may define an inner opening 130 configured to receive the anterior tab body 106. The opening 130 may be aligned generally transverse to the central longitudinal axis A of the instrument 10. For example, the opening 130 may be generally perpendicular to the central longitudinal axis A of the instrument 10. The arm 124 may define a shaft through hole 132 in fluid communication with the opening 130. The shaft hole 132 is configured to receive the rotatable shaft 108. As best seen in FIG. 20, the shaft 108 may extend through hole 132 in arm 124 and through anterior tab body 106, thereby securing and controlling movement of the anterior tab body 106.

Figure 14:
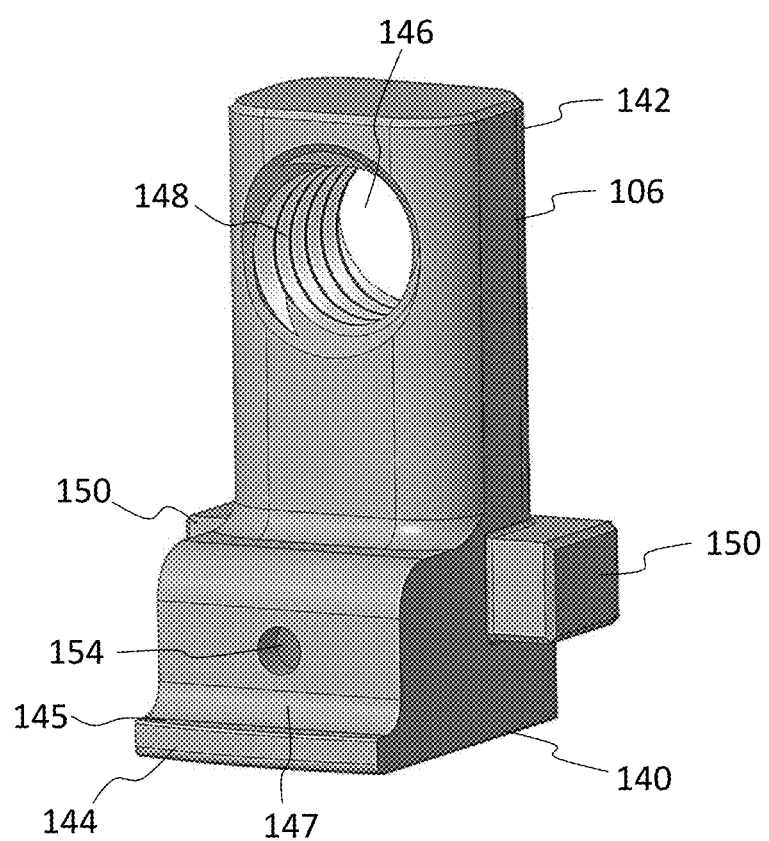
FIG. 14 shows a perspective view the anterior tab body according to one embodiment.

Turning now to FIG. 14, the anterior tab body 106 includes a base 140 with an upwardly or proximally projecting tongue 142. The base 106 includes an anterior tab 144 positioned along the anterior portion of the anterior tab body 106. The anterior tab 144 may be elongated with a length extending in a direction that is generally parallel to a coronal plane of the patient (e.g., a vertical side-to-side extending plane). The anterior tab 144 may extend along the entire width of the anterior tab body 106. The anterior tab 144 is receivable in the corresponding anterior pocket or notch 46 in the tibial tray 14. An upper surface 145 of the anterior tab 144 may be flat or planar. The anterior tab 144 may have a squared-off or angled periphery to thereby hook into the notches 46 in the tibial tray 14. The top 145 of tab 144 may include a curved transition 147 which is generally concave along the length of the base 106. The geometry of the anterior tab 144 may correspond to the smallest tibial tray 14 (e.g., 1T1F size tray). Due to similar geometry amongst all trays 14, the anterior tab 144 is also configured to engage the anterior pocket 46 of all other tray sizes.

The tabs 136, 144 on the inserter 10 are configured to attach to all tray sizes in the set. When the smallest tray 14 is attached (e.g., a size 1T1F tray), the outer geometry of the tabs 134, 144 engage the pockets 44, 46. When the largest size tray 14 is attached (e.g., a size 6T6F tray), the inner geometry of the tabs 134, 144 engages the pockets 44, 46. Any pockets 44, 46 of tray sizes between the smallest and the largest may be engaged by the flat 138, 145 of the tabs 136, 144 which may be a similar feature amongst all tray sizes.

With further emphasis on FIG. 14, the tongue 142 of the anterior tab body 106 projects proximally and is receivable in the opening 130 in the arm 124 of the main body 102 of the instrument 10. A through hole 146 is provided through the tongue 142. The through hole 146 may be internally threaded with one or more threads 148 that correspond to the threads 162 of the shaft 108. The threads 148 of the through hole 146 work in tandem with rotation of the shaft 108, thereby allowing the tab body 106 to translate along the anterior-posterior aspect. In one embodiment, the hole 146 is a triple lead threaded hole configured to interface with a triple lead shaft 108 to thereby increase translation speed of the anterior tab body 106. Different combinations of thread type and single, double, or triple lead threads may be utilized to adjust translation speed to a desired specification.

The anterior tab body 106 may include one or more keyway wings 150. In one embodiment, the base 140 includes a pair of keyway wings 150 projecting outwardly in opposite directions. The keyway wings 150 may extend laterally outward in a direction that is generally parallel to a coronal plane of the patient (e.g., a vertical side-to-side extending plane). Each keyway wing 150 may have a generally polyhedron body with polygonal faces and straight edges. For example, the keyway wing 150 may have the shape of a cube or cuboid, although it will be appreciated that other suitable shapes and configurations may be selected. The wings 150 may be sized and shaped to fit with corresponding grooves or recesses 152 defined in the foot 120 of the main body 102. The keyway wings 150 may be positioned proximally relative to the anterior tab 144 and below the tongue 142. The keyway wings 150 are configured to fit into the keyway groove 134 within the main body 102 to prevent anterior-posterior angulation while expansion occurs. For example, the keyway 134 in the main body 102 may keep the anterior tab body 106 from angulating in the anterior-posterior aspect at a moment about the center of the triple lead hole 146.

Figure 15:
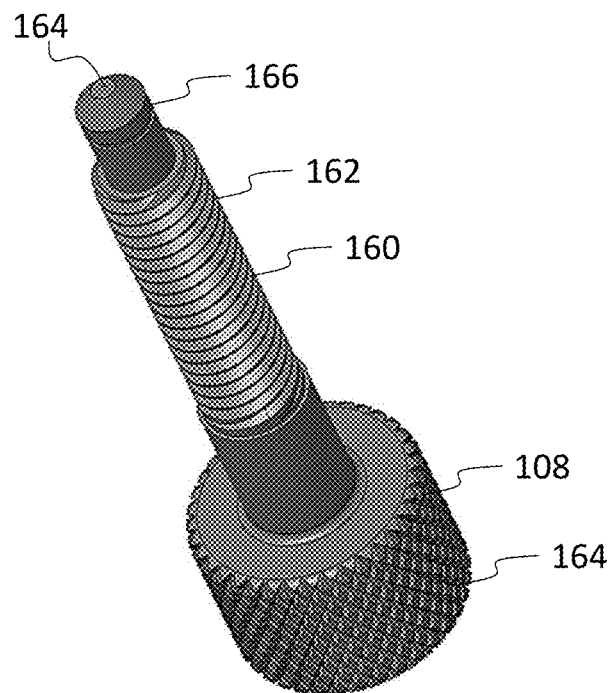
FIG. 15 shows a perspective view of a shaft configured to translate the anterior tab body according to one embodiment.

Turning now to FIG. 15, the shaft 108 works in tandem with the anterior tab body 106 to create translational movement in the anterior-posterior aspect for the tab body 106 to adjust to all tray sizes. The shaft 108 includes a shaft body 160 with one or more threads 162 extending along its length. In an exemplary embodiment, the threads 162 include a triple lead thread configured to mate with corresponding triple lead threads 148 in the hole 146 through the anterior tab body 106. As the shaft 108 rotates, the anterior tab body 106 translates along the anterior-posterior direction, thereby allowing the anterior tab 144 to engage the anterior pocket 46 in the locked configuration. Different combinations of thread type and single/double/triple lead threads may be utilized to adjust translation speed to a desired specification. One end of the shaft 160 may have an enlarged knob 164 configured to be gripped by a user. The enlarged knob 164 may have a coarse knurl or other friction-enhanced surface which aids a scrub technician or surgeon in torqueing down and locking or unlocking the anterior tab 144 into position in the tray 14. A groove 166 is located on the opposite end of the shaft 160 near the tip 168, which is where external retaining ring 170 is fastened after all parts are fully assembled to lock the assembly together.

Figure 16:
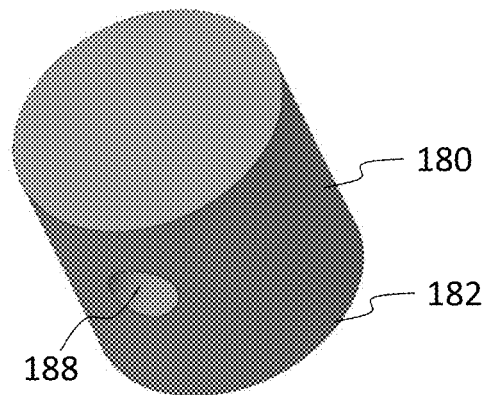
FIG. 16 shows a perspective view of one of the plastic plugs configured to prevent metal on metal contact between the inserter and the tibial tray according to one embodiment.

Turning now to FIG. 16, one or more plugs 180 may be configured to protrude slightly to ensure the bottom planar surface 135 of the main body 102 does not directly contact the proximal face 22 of the tray 14. In one embodiment, the inserter 10 includes three plugs 180: two in the foot 120 on opposite sides of the keyway 134 and one in the base 140 of the anterior tab body 106. The plugs 180 may be comprised of plastic to avoid metal-on-metal contact which may damage the tibial tray 14 and create unwanted stress risers. The plug 180 may have a generally cylindrical body with a flat lower face 182 configured to contact the proximal face 22 of the plate 20 when the instrument 10 is received in the tray 14. The plastic plugs 180 may be press fit into two holes 184 located in the main body 102 and one hole 184 located in the anterior tab body 106. Each of the plastic plugs 180 may be secured with a dowel pin 186 extending through opening 188 in the plug body. For the anterior tab body 106, the pin 186 may be received through transverse opening 154 in the base 140 of the anterior tab body 106. Similarly, each pin 186 may be received through transverse opening 154 in the foot 120 of the main body 102. Each dowel pin 186 may be inserted and blended flush to ensure no loosening of the plug 180 occurs with use of the inserter 10 over time. In the embodiment shown, each dowel pin 186 may be permanently fixed.

When assembled, the anterior tab body 106 is inserted into the opening 130 and keyway 134 in main body 102. The anterior tab body 106 is permitted to translate in opening 130 and keyway 134 along the anterior-posterior direction in order to expand the anterior tab 144 outwardly into the anterior pocket 46 of the tibial tray 14. An insert 172 may limit the total amount of relative translation of the anterior tab body 106. The shaft 108 is threaded through both bodies 102, 106 until fully expanded. The shaft 160 extends through main body 102 and anterior tab body 106. Portions of the shaft 160 contacting the main body 102 may be unthreaded or threaded. The portion of the shaft 160 engaged with the anterior tab body 106 may be threadedly connected thereto to translate the anterior tab body 106. The shaft 108, and in turn the anterior tab body 106, may be locked into place utilizing external retaining ring 170. A first plug 180 may be inserted into opening 184 through the lower face of the base 140 of the anterior tab body 106 and second and third plugs 180 may be inserted into respective openings 184 through the lower face 135 in the foot 120 of the main body 102. Each of the plugs 180 may be secured in position with a dowel pin 186. The plugs 180 protrude downwardly or distally to prevent damage to the tray 14.

Figure 17:
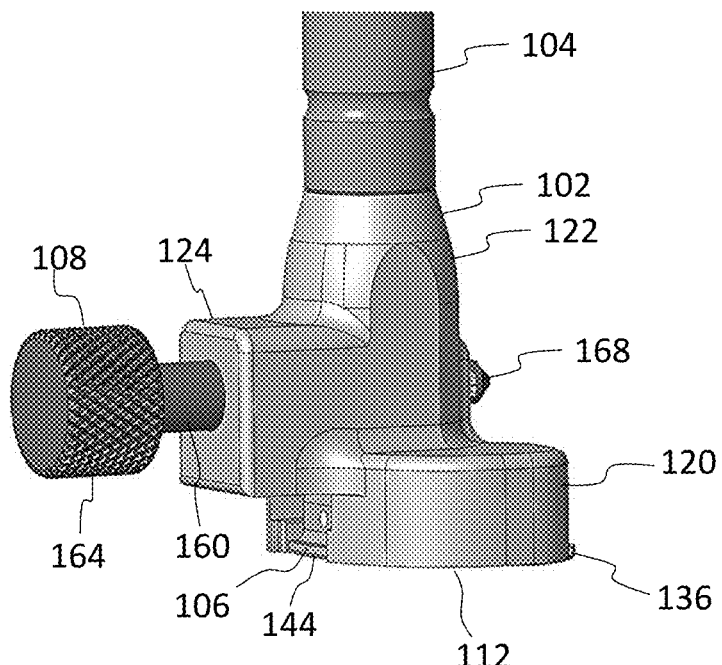
FIG. 17 shows a perspective view of the inserter instrument of FIG. 10 in an unlocked or retracted position.
Figure 18:
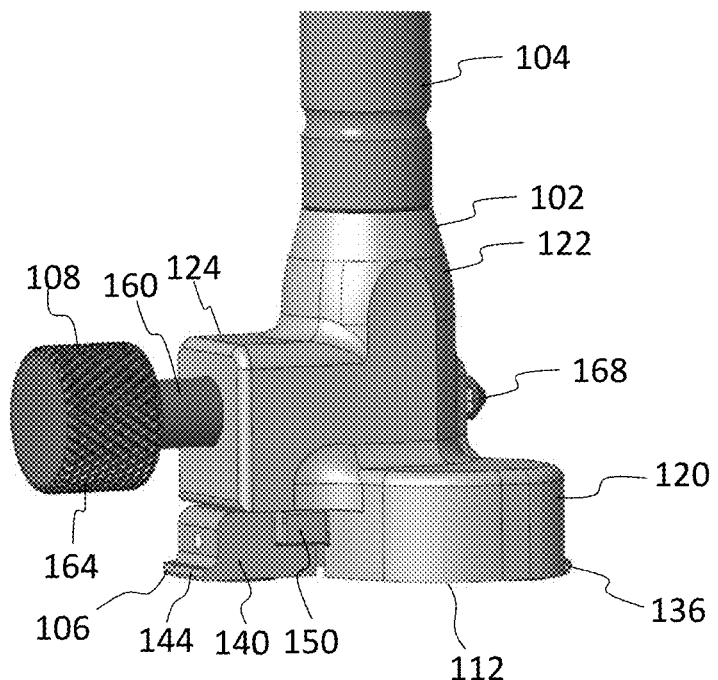
FIG. 18 shows a perspective view of the inserter instrument of FIG. 10 in a locked or expanded position.

FIG. 17 shows the anterior tab body 106 including anterior tab 144 in the retracted or unlocked position. FIG. 18 shows the anterior tab body 106 including anterior tab 144 in the expanded or locked position. As is evident, the anterior tab body 106 is able to translate through keyway 134 in the main body 102 between the unlocked to locked positions.

Figure 19:
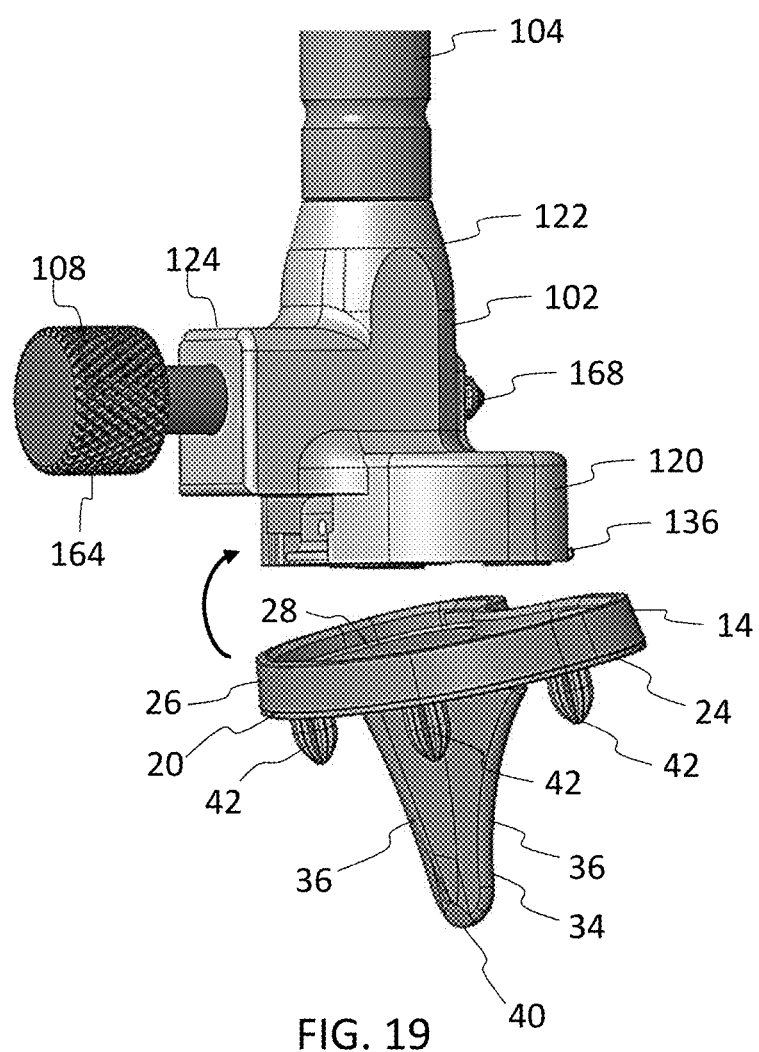
FIG. 19 shows attachment of the inserter to the tibial tray according to one embodiment.

In the retracted position shown in FIG. 19, the anterior tab body 106 is positioned within the keyway 134 and fully housed within the foot 120 of the main body 102. The tibial tray 14 is tipped upward to allow the fixed posterior tabs 136 to engage the posterior notches 44 in the tibial tray 14. After the foot 120 of the main body 102 is fully seated in the insert-receiving space 28, the anterior tab 144 may be locked to the tray 14. As the shaft 108 is rotated as shown in FIG. 20, the anterior tab body 106 slides outward in the anterior direction. The keyway wings 150 on the anterior tab body 106 prevent anterior-posterior angulation while expansion occurs. In the expanded position, the anterior tab body 106 protrudes outwardly, thereby allowing the anterior tab 144 to engage the anterior notch 46 in the tibial tray 14 and lock the inserter 10 to the tibial tray 14.

Figure 22:
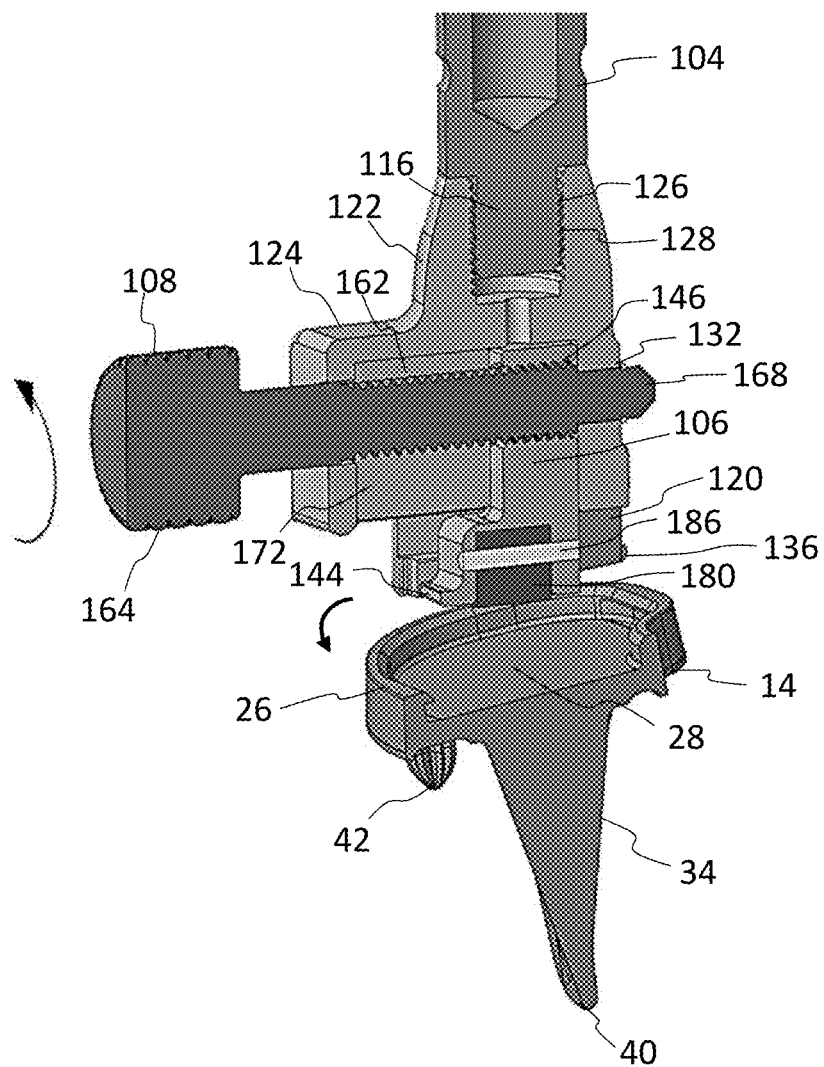
FIG. 22 is a cross-sectional view of the inserter with the anterior tab retracted thereby unlocking and removing the tibial tray from the inserter.

FIG. 22 shows retraction of the anterior tab body 106 and removal of the instrument 10 from the tray 14. The shaft 108 is rotated in the opposite direction, thereby releasing the anterior tab 144 from the anterior notch of the tibial tray 14. The tibial tray 14 is tipped downwardly to release the fixed posterior tabs 136 and free the instrument 10 from the tray 14. The insert 16 may now be positioned in and locked to the tibial tray 14 utilizing same the anterior and posterior notches 44, 46 in the tibial tray 14.

Figure 23:
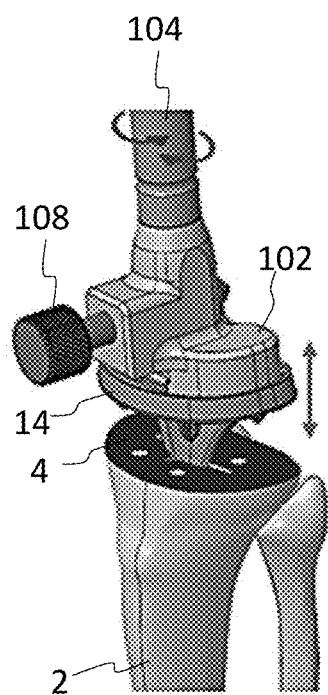
FIGS. 23-25 show perspective, lateral, and anterior views, respectively, of the tibial tray implantation to the proximal tibia including control over six degrees of freedom of movement via the inserter.
Figure 24:
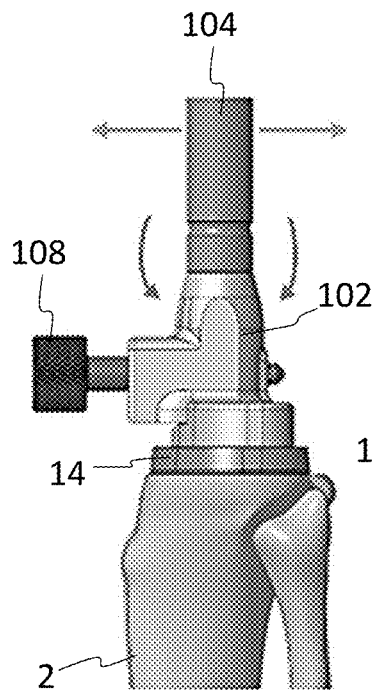
Figure 25:
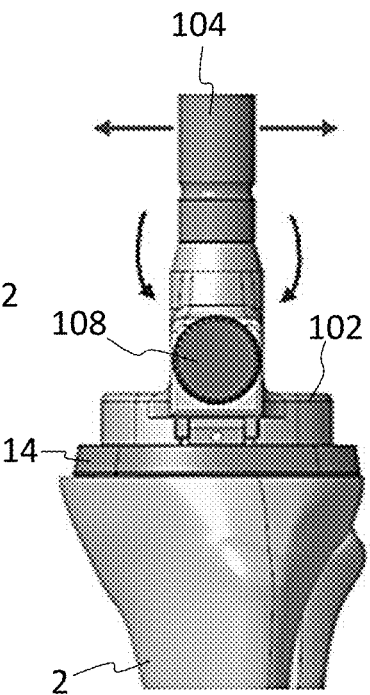

FIGS. 23-25 show control over six degrees of freedom of movement via the inserter 10. FIG. 23 shows curved arrows around the handle 104 representing internal/external rotation and straight arrows next to the tibial tray 14 representing proximal/distal translation. FIG. 24 shows straight arrows next to the handle 104 representing anterior/posterior translation and curved arrows next to the main body 102 representing anterior/posterior angulation. FIG. 25 shows straight arrows next to the handle 104 representing medial/lateral translation and curved arrows next to the main body 102 representing varus/valgus angulation. The lockable functionality of the inserter instrument 10 to the tibial tray 14 allows for control over six degrees of freedom of movement and precise placement of the tibial tray 14 during implantation.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A system for a knee arthroplasty, the system comprising:
   a tibial tray having a perimeter wall defining an insert-receiving space, the perimeter wall defining a pair of posterior notches and a single anterior notch; and
   an inserter having a main body with a pair of fixed posterior tabs, a moveable anterior tab body having an anterior tab, and a rotatable shaft for controlling movement of the anterior tab body, wherein the posterior tabs are receivable in the posterior notches of the tibial tray and the anterior tab is receivable in the anterior notch of the tibial tray when the shaft is rotated and the anterior tab body is translated into an expanded position
   wherein the main body of the inserter includes a foot with a neck protruding upwardly and an arm protruding anteriorly, wherein the foot is bifurcated by a keyway, and the anterior tab body is receivable in the keyway
   wherein the anterior tab body includes a pair of keyway wings projecting outwardly in opposite directions, wherein the keyway defines recesses configured to receive the respective keyway wings, thereby preventing anterior-posterior angulation while expansion occurs.

2. The system of claim 1, wherein the tibial tray has a kidney-bean shape with an anterior side forming an outer convex side and a posterior side including an inner concave side separating two lobes.

3. The system of claim 1, wherein the tibial tray includes a keel attached to a distal surface of the tibial tray, and the keel includes a pair of coronal fins and at least one sagittal fin.

4. The system of claim 1, wherein the inserter includes a plurality of plugs press fit into the main body and the anterior tab body, wherein the plurality of plugs protrude from a bottom of the main body, thereby ensuring the main body does not contact the insert-receiving space of the tibial tray.

5. An inserter instrument for implanting a tibial tray, the instrument comprising:
   a main body coupled to a handle, the main body including a pair of posterior tabs;
   a moveable anterior tab body inside the main body, the anterior tab body including a threaded opening and an anterior tab; and
   a rotatable shaft for controlling movement of the anterior tab body, the shaft having a threaded portion engaged with the threaded opening in the anterior tab body, the shaft positioned through the main body and the anterior tab body, wherein when the shaft is rotated, the anterior tab body is translated outside the main body into a locked position
   wherein the main body includes a foot with a neck protruding upwardly and an arm protruding anteriorly
   wherein the foot is bifurcated by a keyway, and the anterior tab body is receivable in the keyway,
   wherein the anterior tab body includes a pair of keyway wings projecting outwardly in opposite directions, wherein the keyway defines recesses configured to receive the respective keyway wings, thereby preventing anterior-posterior angulation while expansion occurs.

6. The inserter instrument of claim 5, wherein the foot has an outer kidney-bean shape.

7. The inserter instrument of claim 5, wherein the anterior tab body includes a base with an upwardly projecting tongue, and the tongue defines the threaded opening.

8. The inserter instrument of claim 7, wherein the threaded opening is a triple lead threaded hole, and the shaft includes a triple lead shaft configured to interface with the triple lead threaded hole to increase translation speed of the anterior tab body.

9. The inserter instrument of claim 7, wherein the anterior tab is positioned along an anterior portion of the base, wherein the anterior tab extends along the entire width of the anterior tab body.

10. The inserter instrument of claim 5, wherein the handle includes an elongate body that terminates distally at a threaded end, wherein the threaded end mates with corresponding threads in the main body.

\* \* \* \* \*